United States Patent
Subramaniyam

(10) Patent No.: US 9,598,333 B2
(45) Date of Patent: *Mar. 21, 2017

(54) ADDITIVE COMPOSITION FOR CONTROL AND INHIBITION OF POLYMERIZATION OF ALIPHATIC MONOMERS, AND METHODS OF PREPARATION AND USE THEREOF

(71) Applicant: Dorf Ketal Chemicals (India) Private Limited, Mumbai (IN)

(72) Inventor: Mahesh Subramaniyam, Mumbai (IN)

(73) Assignee: Dorf Ketal Chemicals (India) Private Limited, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/779,843

(22) PCT Filed: Mar. 20, 2014

(86) PCT No.: PCT/IB2014/059998
§ 371 (c)(1),
(2) Date: Sep. 24, 2015

(87) PCT Pub. No.: WO2014/155248
PCT Pub. Date: Oct. 2, 2014

(65) Prior Publication Data
US 2016/0083315 A1    Mar. 24, 2016

(30) Foreign Application Priority Data

Mar. 26, 2013 (IN) .......................... 1165/MUM/2013

(51) Int. Cl.
| C07B 63/04 | (2006.01) |
| C07C 7/20 | (2006.01) |
| C07C 11/167 | (2006.01) |
| C09K 15/30 | (2006.01) |
| C09K 15/22 | (2006.01) |

(52) U.S. Cl.
CPC .............. C07C 7/20 (2013.01); C07B 63/04 (2013.01); C09K 15/22 (2013.01); C09K 15/30 (2013.01)

(58) Field of Classification Search
None
See application file for complete search history.

(56) References Cited

U.S. PATENT DOCUMENTS

| 5,290,888 A * | 3/1994 | Gatechair | C07C 7/20 526/83 |
| 6,403,850 B1 * | 6/2002 | Benage | C07B 63/04 208/48 AA |
| 6,673,879 B2 * | 1/2004 | Shahid | C07B 63/04 526/227 |
| 8,766,027 B1 * | 7/2014 | Subramaniyam | C07C 7/20 585/4 |
| 9,217,107 B2 * | 12/2015 | Subramaniyam | C07B 63/04 |
| 9,228,126 B2 * | 1/2016 | Subramaniyam | C07B 63/04 |
| 9,234,057 B2 * | 1/2016 | Subramaniyam | C07C 7/20 |
| 9,334,445 B2 * | 5/2016 | Subramaniyam | C07C 7/20 |
| 2004/0010159 A1 * | 1/2004 | Benage | C07B 63/04 558/306 |
| 2006/0155140 A1 * | 7/2006 | Benage | C07B 63/04 560/4 |
| 2008/0269383 A1 * | 10/2008 | Pauquet | C08K 5/527 524/120 |
| 2009/0114878 A1 * | 5/2009 | Weyler | C07C 7/20 252/182.29 |

(Continued)

FOREIGN PATENT DOCUMENTS

| IN | 1165MUM2013 | 3/2013 |
| WO | 0233026 A1 | 4/2002 |

(Continued)

OTHER PUBLICATIONS

Foreign communication from the priority application—International Search Report and Written Opinion, PCT/IB2014/059998, Jul. 18, 2014, 10 pages.

(Continued)

Primary Examiner — Joseph D Anthony
(74) Attorney, Agent, or Firm — Conley Rose, P.C.; Rodney B. Carroll

(57) ABSTRACT

The present invention relates to additive composition and method of use thereof for controlling and inhibition of polymerization and dimerization of aliphatic monomers including butadiene comprising A) one or more of first component selected from a group comprising a) quinone methide (QM), b) quinone methide (QM) derivative including ester derivative of quinone methide, c) nitroxide (i.e. nitroxyl) compounds, and d) mixture thereof; characterized in that the composition further comprises B) one or more of second component selected from amines or polyamines, wherein the amine and polyamine is selected from a group comprising i) oxide treated tertiary amines, ii) hydroxyl alkyl tertiary amines, iii) polyether amines, and iv) mixture thereof. In one embodiment, the present invention also relates to a method for controlling and inhibiting polymerization and dimerization of aliphatic monomers including butadiene by employing the presently provided compositions, and in another embodiment, the present invention relates to a method of preparation of the presently provided compositions.

23 Claims, No Drawings

(56) References Cited

U.S. PATENT DOCUMENTS

| | | | | |
|---|---|---|---|---|
| 2012/0101295 A1* | 4/2012 | Weyler | .................... | C07C 7/20 560/2 |
| 2014/0200375 A1* | 7/2014 | Subramaniyam | ......... | C07C 7/20 585/5 |
| 2014/0364660 A1* | 12/2014 | Subramaniyam | ......... | C07C 7/20 585/4 |

FOREIGN PATENT DOCUMENTS

| WO | 2013054353 A1 | 4/2013 |
|---|---|---|
| WO | 2013102930 A1 | 7/2013 |
| WO | 2013105113 A1 | 7/2013 |
| WO | 2014030131 A1 | 2/2014 |
| WO | 2014155248 A1 | 10/2014 |

OTHER PUBLICATIONS

Foreign communication from the priority application—International Preliminary Report on Patentability, PCT/IB2014/059998, Jun. 10, 2015, 17 pages.

* cited by examiner

ADDITIVE COMPOSITION FOR CONTROL AND INHIBITION OF POLYMERIZATION OF ALIPHATIC MONOMERS, AND METHODS OF PREPARATION AND USE THEREOF

CROSS-REFERENCE TO RELATED APPLICATIONS

This application is a filing under 35 U.S.C. 371 of International Application No. PCT/IB2014/059998 filed Mar. 20, 2014, entitled "Additive Composition for Control and Inhibition of Polymerization of Aliphatic Monomers, and Methods of Preparation and Use Thereof," which claims priority to Indian Patent Application No. 1165/MUM/2013 filed Mar. 26, 2013, which applications are incorporated by reference herein in their entirety.

FIELD OF THE INVENTION

The present invention relates to additive composition for control and inhibition of polymerization of aliphatic monomers including butadiene, wherein the composition comprises:
- A) one or more of first components selected from a group comprising
  - a) quinone methide (QM), quinone methide (QM) derivative including ester derivative of quinone methide,
  - b) nitroxide (i.e. nitroxyl) compounds, and
  - c) mixture thereof; characterized in that the composition further comprises
- B) one or more of second components selected from amines and polyamines, wherein the amine and polyamine is selected from a group comprising:
  - i) oxide treated tertiary amines,
  - ii) hydroxyl alkyl tertiary amines,
  - iii) polyether amines, and
  - iv) mixture thereof.

In one embodiment, the present invention relates to the use of said composition of the present invention to control and inhibit polymerization of butadiene.

In another embodiment, the present invention relates to the method of preparation of said composition of the present invention for control and inhibition of polymerization of butadiene.

In still another embodiment, the present invention relates to the method of controlling and inhibiting polymerization of butadiene by employing said composition of the present invention, wherein the stream containing butadiene is treated with said composition of the present invention.

BACKGROUND OF THE INVENTION

The polymerization of butadiene during processing of hydrocarbons is a matter of concern, because it causes formation of unwanted polymers and results in loss of yield of end product and makes the process un-economical. Further, the butadiene also gets dimerized, which further enhances the wastage, and thereby, further enhances cost of production.

The prior art discloses use of quinone methide (QM) or its derivatives including 4-benzylidene-2,6-di-tert-butylcyclohexa-2,5-dienone, and use of nitroxide (i.e. nitroxyl) compounds including 1 oxyl-2,2,6,6-tetramethylpiperidin-4-ol or 4-hydroxy-2,2,6,6-tetramethylpiperidin-1-oxyl (or 4 Hydroxy Tempo or 4HT) as polymerization inhibitor. The PCT publication no. WO 2002/33026 (PCT/US2001/30954) and US publication no. US 2009/0114878A1 disclose combination of quinone alkide/methide and nitroxyl compounds. However, the inventor has found [refer to examples] that main problem of using the QM or its derivatives, or nitroxides including 4HT is that these have to be used in higher amounts to achieve commercially acceptable level (acceptable by the industry) of inhibition, and such higher amount not only results in increase of cost of the process, but also results in formation of undesired products due to unstable nature of QM or its derivatives and nitroxides including 4HT.

Therefore, the industry is aiming for additive composition wherein the dosage of components of compositions of the prior art, particularly of the QM or its derivatives, and the nitroxides (i.e. nitroxyl) compounds including 4HT can be minimized or reduced. Any effort in the direction of lowering the consumption of these components will lessen the problem of industry, and the resulted composition will be economical as well as safe for human being.

NEED OF THE INVENTION

Therefore, there is still a need of an effective additive composition and method of its use and preparation, and method of controlling and inhibiting polymerization of aliphatic monomers including butadiene, and for control and inhibition of dimerization of aliphatic monomers including butadiene by employing said composition, wherein the additive composition is not only suitable for substantial control and inhibition of polymerization of butadiene, but is also suitable for control and inhibition of dimerization of aliphatic monomers including butadiene, and also comprises substantially reduced or minimized amount of the QM or its derivatives, and the nitroxides (i.e. nitroxyl) compounds.

PROBLEM TO BE SOLVED BY THE INVENTION

Therefore, the present invention aims at providing a solution to the above-described existing industrial problems by providing effective additive composition and method of its use and preparation, and method of controlling and inhibiting polymerization of aliphatic monomers including butadiene, and for control and inhibition of dimerization of aliphatic monomers including butadiene, wherein the additive composition is not only suitable for substantial control and inhibition of polymerization of butadiene, but is also suitable for control and inhibition of dimerization of aliphatic monomers including butadiene, and also comprises substantially reduced or minimized amount of the QM or its derivatives, and nitroxides (i.e. nitroxyl) compounds.

OBJECTS OF THE INVENTION

Accordingly, the main object of present invention is to provide an effective additive composition, and methods of its use and preparation, and method of controlling and inhibiting polymerization of aliphatic monomers including butadiene, and for control and inhibition of dimerization of aliphatic monomers including butadiene, wherein the additive composition is not only suitable for substantial control and inhibition of polymerization of butadiene, but is also suitable for control and inhibition of dimerization of aliphatic monomers including butadiene, and also comprises substantially reduced or minimized amount of one or more of compounds (which may be referred to as 'first component' or as 'component A' or as 'compound A') selected from a group comprising QM or its derivatives, and nitroxides (i.e. nitroxyl) compounds including 1-oxyl-2,2,6,6-tetramethylpiperidin-4-ol or 4-hydroxy-2,2,6,6-tetramethylpiperidin-1-oxyl (or 4 Hydroxy Tempo or 4HT, hereinafter may be referred to as 4HT), and mixture thereof.

Another main object of the present invention is to provide the above-described said additive composition, and methods of its use and preparation, and method of controlling and inhibiting polymerization, and dimerization of aliphatic monomers including butadiene, wherein the additive composition is required in relatively lower dosage as compared to dosage of compositions of the prior art comprising one or more of the compounds selected from a group comprising QM or its derivatives, and nitroxides (i.e. nitroxyl) compounds including 4HT, and mixture thereof for achieving the same or better commercially acceptable level of control and inhibition of polymerization, and dimerization of aliphatic monomers including butadiene.

This is also an object of the present invention to provide the above-described said additive composition, and methods of its use and preparation, and method of controlling and inhibiting polymerization, and dimerization of aliphatic monomers including butadiene, wherein the additive composition comprises reduced or minimized amount of one or more of the compounds (which may be referred to as 'first component' or as 'component A' or as 'compound A') selected from a group comprising quinone methide (QM) or its derivatives including ester derivatives of quinone methide, and nitroxide (i.e. nitroxyl) compounds including 4HT, and mixture thereof; and it further comprises one or more of compounds, which may be referred to as 'second component' or as 'component B' or as 'compound B' selected from amines or polyamines.

Other objects and advantages of the present invention will become more apparent from the following description when read in conjunction with examples, which are not intended to limit scope of the present invention.

BRIEF DESCRIPTION AND SUMMARY OF THE INVENTION

The present invention primarily aims at providing an additive composition, and methods of its use and preparation, and method of controlling and inhibiting polymerization, and dimerization of aliphatic monomers including butadiene, wherein the additive composition comprises reduced or minimized amount of:
   one or more of first component selected from a group comprising
      a) quinone methide (QM),
      b) quinone methide (QM) derivative including ester derivative of quinone methide,
      c) nitroxide (i.e. nitroxyl) compounds, and
      d) mixture thereof;
   characterized in that it further comprises one or more of second component selected from amines or polyamines, wherein the amine and polyamine is selected from a group comprising
      i) oxide treated tertiary amines,
      ii) hydroxyl alkyl tertiary amines,
      iii) polyether amines, and
      iv) mixture thereof, and
   therefore, the composition of the present invention is not only economical, but is also environment friendly.

Accordingly, the present invention also aims at improving the performance of compounds selected from a group comprising QM or its derivatives, and nitroxides (i.e. nitroxyl) compounds including 4HT, and mixture thereof at a wider range of temperature including the higher temperature.

Accordingly, the present invention also aims at improving the performance of compounds selected from a group comprising QM or its derivatives, and nitroxides (i.e. nitroxyl) compounds including 4HT, and mixture thereof at a wider range of temperature including the higher temperature and in presence of air.

DESCRIPTION OF THE INVENTION

With aim to overcome above-described problems of the prior art and to achieve the above-described objects of the present invention, the inventor has found that when one or more of the amines or polyamines selected from a group comprising
   i) oxide treated tertiary amines,
   ii) hydroxyl alkyl tertiary amines,
   iii) polyether amines, and
   iv) mixture thereof,
is added to the composition comprising the compound (first component) selected from a group comprising QM or its derivatives, and nitroxides (i.e. nitroxyl) compounds including 4HT, and mixture thereof, then not only polymerization and dimerization controlling and inhibiting efficiency of the compound (first component) is substantially improved, but polymerization and dimerization of aliphatic monomers including butadiene is, surprisingly and unexpectedly, also controlled and inhibited to the industrially acceptable level with substantially reduced and minimized dosage of the first components, which makes the present composition economical as well as environment friendly.

Accordingly, the present invention relates to an additive composition for control and inhibition of polymerization and dimerization of aliphatic monomers including butadiene comprising:
   A) one or more of first component selected from a group comprising
      a) quinone methide (QM),
      b) quinone methide (QM) derivative including ester derivative of quinone methide,
      c) nitroxide (i.e. nitroxyl) compounds, and
      d) mixture thereof;
   characterized in that the composition further comprises
   B) one or more of second component selected from amines or polyamines, wherein the amine and polyamine is selected from a group comprising:
      i) oxide treated tertiary amines,
      ii) hydroxyl alkyl tertiary amines,
      iii) polyether amines, and
      iv) mixture thereof.

In accordance with one of the preferred embodiments of the present invention, the oxide treated tertiary amine, which may be referred to as oxide treated polymeric amine of propylene oxide treated amine includes N,N,N',N'-Tetrakis (2-hydroxypropyl) ethylene-diamine) (Quadrol®).

In accordance with one of the preferred embodiments of the present invention, the hydroxyl alkyl tertiary amine, which may be referred to as oxide treated polymeric amine of hydroxyl alkyl tertiary amine includes tris(2-hydroxypropyl)amine (TIPA).

Accordingly, in accordance with one of the preferred embodiments, the present invention relates to additive composition for controlling and inhibition of polymerization and dimerization of aliphatic monomers including butadiene comprising:

A) one or more of first component selected from a group comprising
   a) quinone methide (QM),
   b) quinone methide (QM) derivative including ester derivative of quinone methide,
   c) nitroxide (i.e. nitroxyl) compounds, and
   d) mixture thereof;
characterized in that the composition further comprises
B) one or more of second component selected from amines or polyamines, wherein the amine and polyamine is selected from a group comprising:
   i) oxide treated tertiary amines,
   ii) hydroxyl alkyl tertiary amines,
   iii) polyether amines, and
   iv) mixture thereof,
   wherein the oxide treated tertiary amine includes N,N,N',N'-Tetrakis (2-hydroxypropyl) ethylene-diamine) (Quadrol®), and
   the hydroxyl alkyl tertiary amines includes tris(2-hydroxypropyl)amine (TIPA).

In present description above first component may be referred to as component A of the present composition and the above second component may be referred to as component B of the present composition.

In accordance with one of the preferred embodiments of the present invention, the nitroxide (i.e. nitroxyl) compounds include 1-oxyl-2,2,6,6-tetramethylpiperidin-4-ol or 4-hydroxy-2,2,6,6-tetramethylpiperidin-1-oxyl (or 4 Hydroxy Tempo or 4HT, hereinafter may be referred to as 4HT).

It has been found that when composition of the present invention comprises one or more said amines or polymeric amines (component B), the efficiency of said component A to control and inhibit polymerization and dimerization of aliphatic monomers including butadiene is, surprisingly and unexpectedly, substantially improved to the acceptable level that's too at substantially reduced or minimized dosages of said component A, thereby making the composition of the present invention relatively more economical and environment friendly.

In accordance with one of the embodiments of the present invention, the composition of present invention comprises:
   a) about 40 to about 99.75% by weight of I) one or more of said compounds (component A); and
   b) about 0.25 to about 60% by weight of II) said amines or polymeric amines or mixture thereof (component B).

In accordance with one of the preferred embodiments of the present invention, amount of the composition of the present invention added to the stream containing butadiene is selected from the group comprising varying from about 0.01 ppm to about 2000 ppm, and from about 1 ppm to about 2000 ppm by weight of the stream of the monomers including butadiene.

It may be noted that the butadiene may be present in the stream along with other monomers. The present invention is applicable to control and inhibit polymerization of aliphatic monomers including butadiene, and to control and inhibit dimerization of aliphatic monomers including butadiene but excluding aromatic monomers.

Accordingly, in another embodiment, the present invention also relates to method of using said additive composition of the present invention, described herein, a reference to which is drawn in entirety, to control and inhibit polymerization and dimerization of aliphatic monomers including butadiene, wherein to the stream comprising monomers including butadiene said additive composition comprising one or more of said component A and one or more of said component B is added.

In particular, in second embodiment, the present invention relates to a method of using said additive composition of the present invention, described herein, a reference to which is drawn in entirety, for controlling and inhibition of polymerization and dimerization of aliphatic monomers including butadiene, wherein to the stream comprising the aliphatic monomers including the butadiene and excluding aromatic monomers, the additive composition comprising:

A) one or more of component A selected from a group comprising
   a) quinone methide (QM),
   b) quinone methide (QM) derivative including ester derivative of quinone methide,
   c) nitroxide (i.e. nitroxyl) compounds, and
   d) mixture thereof;
characterized in that the composition further comprising
B) one or more of component B selected from amines or polyamines, wherein said amine and polyamine is selected from a group comprising:
   i) oxide treated tertiary amines,
   ii) hydroxyl alkyl tertiary amines,
   iii) polyether amines, and
   iv) mixture thereof,
   is added.

In accordance with one of the embodiments of the present invention, the oxide treated tertiary amine includes N,N,N',N'-Tetrakis (2-hydroxypropyl) ethylene-diamine) (Quadrol®).

In accordance with one of the embodiments of the present invention, the hydroxyl alkyl tertiary amines includes tris (2-hydroxypropyl)amine (TIPA).

In accordance with one of the embodiments of the present invention, the method of using said additive composition of the present invention comprises adding amount selected from the group comprising varying from about 0.01 ppm to about 2000 ppm, and from about 1 ppm to about 2000 ppm of said composition to the monomer stream including butadiene and excluding aromatic monomers based on weight of the monomers.

In accordance with one of the preferred embodiments of the present invention, one or more of the component A and one or more of the component B are added to the monomers stream either individually or after mixing.

It may be noted that all the features of the compositions of the present invention described herein, a reference to which is drawn in entirety, are deemed to have been included in the present method of using said additive compositions of the present invention.

Accordingly, in third embodiment, the present invention also relates to a method for controlling and inhibiting polymerization and dimerization of aliphatic monomers including butadiene and excluding aromatic monomers by employing said additive composition of the present invention, described herein, a reference to which is drawn in entirety, wherein the stream comprising monomers including butadiene and excluding aromatic monomers is treated with the additive composition of the present invention comprising one or more of said component A and one or more of said component B.

In particular, in third embodiment, the present invention relates to a method for controlling and inhibition of polymerization and dimerization of aliphatic monomers including butadiene and excluding aromatic monomers, wherein said monomers are treated with the additive composition of the present invention, described herein, a reference to which is drawn in entirety, and wherein the additive composition comprises:

A) one or more of component A selected from a group comprising
  a) quinone methide (QM),
  b) quinone methide (QM) derivative including ester derivative of quinone methide,
  c) nitroxide (i.e. nitroxyl) compounds, and
  d) mixture thereof;
characterized in that the composition further comprising
B) one or more of component B selected from amines or polyamines, wherein said amine and polyamine selected from a group comprising:
  i) oxide treated tertiary amines,
  ii) hydroxyl alkyl tertiary amines,
  iii) polyether amines, and
  iv) mixture thereof.

In accordance with one of the embodiments of the present invention, the oxide treated tertiary amine includes N,N,N',N'-Tetrakis (2-hydroxypropyl) ethylene-diamine) (Quadrol®).

In accordance with one of the embodiments of the present invention, the hydroxyl alkyl tertiary amines includes tris (2-hydroxypropyl)amine (TIPA), In accordance with one of the preferred embodiments of the present invention, the method for controlling and inhibition of polymerization and dimerization of aliphatic monomers including butadiene and excluding aromatic monomers by employing said additive compositions of the present invention comprises adding an amount selected from the group comprising varying from about 0.01 ppm to about 2000 ppm, and from about 1 ppm to about 2000 ppm of the compositions to the monomers stream including butadiene based on weight of the monomers.

In accordance with one of the preferred embodiments of the present invention, one or more of the component A and one or more of the component B are added to the monomers stream either individually or after mixing.

It may be noted that all the features of the compositions of the present invention described herein, a reference to which is drawn in entirety, are deemed to have been included in the present method for controlling and inhibition of polymerization and dimerization of aliphatic monomers including butadiene by employing said additive compositions of the present invention.

In accordance with one of the embodiments of the present invention, the composition of the present invention may be mixed with the stream containing monomers including butadiene and excluding aromatic monomers either before the stream enters into processing system or after the stream has entered into processing system, but preferably the composition is added to the stream containing monomers including butadiene before its processing starts so that polymerization and dimerization of aliphatic monomers including butadiene is avoided or minimized.

In accordance with one of the embodiments of the present invention, the present composition may be used over a wide range of temperature selected from the group comprising varying from about 50 degree C. to about 180 degree C., and from about 60 degree C. to about 180 degree C.

The additive compositions of the present invention may be prepared in any known manner to prepare the compositions.

Accordingly, in fourth embodiment, the present invention also relates to a method of preparing additive compositions of the present invention, described herein, a reference to which is drawn in entirety, for controlling and inhibiting polymerization and dimerization of aliphatic monomers including butadiene (and excluding aromatic monomers), wherein one or more of the component A are mixed with one or more of said component B either individually or after mixing.

In particular, in fourth embodiment, the present invention relates to a method for preparation of additive compositions of the present invention, described herein, a reference to which is drawn in entirety, for controlling and inhibition of polymerization and dimerization of aliphatic monomers including butadiene and excluding aromatic monomers, wherein said method comprises:

(A) mixing one or more of the component A selected from a group comprising
  a) quinone methide (QM),
  b) quinone methide (QM) derivative including ester derivative of quinone methide,
  c) nitroxide (i.e. nitroxyl) compounds, and
  d) mixture thereof;
characterized in that the compounds are further mixed with
B) one or more of component B selected from amines or polyamines, wherein said amine and polyamine is selected from a group comprising:
  i) oxide treated tertiary amines,
  ii) hydroxyl alkyl tertiary amines,
  iii) polyether amines, and
  iv) mixture thereof.

In accordance with one of the embodiments of the present invention, the oxide treated tertiary amine includes N,N,N',N'-Tetrakis (2-hydroxypropyl) ethylene-diamine) (Quadrol®).

In accordance with one of the embodiments of the present invention, the hydroxyl alkyl tertiary amines includes tris (2-hydroxypropyl)amine (TIPA), In accordance with one of the embodiments of the present invention, the method for preparation of additive composition of the present invention comprises mixing one or more of the component B with one or more of said component A either individually or after mixing.

In accordance with one of the embodiments of the present invention, the composition prepared is used over a range of temperature selected from the group comprising varying from about 50 degree C. to about 180 degree C., and from about 60 degree C. to about 180 degree C.

It may be noted that in accordance with the present invention the stream comprises aliphatic monomers including butadiene and excludes aromatic monomers, and the stream may be referred to as monomer stream or as butadiene stream.

It may also be noted that all the features of the compositions of the present invention, described herein, a reference to which is drawn in entirety, are deemed to have been included in the present method for preparation of the additive compositions of the present invention.

It may be noted that the terms or words "first component" or "first components" or "compounds" or "said compounds" or "compound A" or "compounds A" or "component A" or "components A" used herein are intended to mean and include:

one or more of the compounds selected from a group comprising
  a) quinone methide (QM),
  b) quinone methide (QM) derivative including ester derivative of quinone methide, c) nitroxide (i.e. nitroxyl) compounds, and
d) mixture thereof.

It may be noted that the terms or words "amines" or "said amines" or "polyamines" or "said polyamines" or "second component" or "second components" or "compound B" or "compounds B" or "component B" or "components B" used herein are intended to mean and include:

i) oxide treated tertiary amines,
ii) hydroxyl alkyl tertiary amines,
iii) polyether amines, and
iv) mixture thereof.

Further advantages and embodiments of the present invention will become more apparent from the following examples.

The present invention is now described with the help of following examples, which are not intended to limit scope of the present invention, but have been incorporated to illustrate mode and best mode of performing the present invention.

EXPERIMENTS

In following experiments gel is cross linked polybutadiene or simply butadiene polymer or polybutadiene, and dimer is vinyl cyclohexene, which is formed by condensation of two butadiene ring compounds, and the amounts are expressed in % by weight.

Experiment—I.
Condition: Autoclave (100 ml Capacity)
Sample: 1,3-Butadiene
Temperature: 120° C.
Time: 4 hrs
Motor speed: 1000 rpm
Purge gas: Nitrogen (15 kgs Blanketing, pressure at 120° C. is 35-36 kgs)

The above experiment of Invention Composition—1 of Table 1 also confirms that the present composition comprising QM and TIPA additionally controls the dimerization of butadiene. It has been found that the present composition comprising 300 ppm of QM and 75 ppm of TIPA has about 78% efficiency to control the dimerization of butadiene, and the present composition comprising 200 ppm of QM and 50 ppm of TIPA has about 70% efficiency to control the dimerization of butadiene as against only about 47.3% efficiency to control the dimerization of butadiene when prior art additive is used, which confirms additional surprising and unexpected technical advantages of the present composition.

The above experiment of Invention Composition—2 of Table 1 confirms that with addition of just 1.5 ppm of TIPA, only 7.5 ppm of TEMO is required as against 18 ppm of TEMPO to achieve 100% control/inhibition of polymerization of 1,3-butadiene, thereby results in saving of about 10.5 ppm (about 58.33%) of TEMPO confirming surprising and unexpected technical advantages of the present composition.

The above experiment of Invention Composition—2 of Table 1 also confirms that the present composition comprising TEMPO and TIPA additionally controls the dimerization of butadiene. It has been found that with the present composition comprising 200 ppm of TEMPO and 50 ppm of TIPA has about 48.5% efficiency to control dimerization of butadiene, and the present composition comprising 200 ppm of TEMPO and 10 ppm of TIPA has about 36.1% efficiency to control dimerization of butadiene as against no control of the dimerization of butadiene when prior art additive is used, which also confirms additional surprising and unexpected technical advantages of the present composition.

TABLE I

| Additive | Active Dosage (ppm) | Gel (%) | Dimer (%) | Non Volatile (%) | % Efficiency of Polymerization control | % Efficiency of dimerization control |
|---|---|---|---|---|---|---|
| Blank | — | 4.44 | 20.4 | 0.55 | — | — |
| 4-benzylidene-2,6-di-tert-butylcyclohexa-2,5-dienone (QM) - Prior art | 50 | 2.75 | 18.5 | 0.57 | 38 | 9.8 |
|  | 200 | 0 | 10.7 | 0.11 | 100 | 47.3 |
| 4-benzylidene-2,6-di-tert-butylcyclohexa-2,5-dienone (QM) and TIPA (Invention Composition-1) | 12.5 + 2.5 | 1.79 | 21.2 | 0.49 | 59.7 | 0 |
|  | 17 + 1.5 | 0 | 22.15 | 0.22 | 100 | 0 |
|  | 200 + 50 | 0 | 6.12 | 0.37 | 100 | 70 |
|  | 300 + 75 | 0 | 4.4 | 0.75 | 100 | 78 |
| 4-hydroxy-2,2,6,6-tetramethylpiperidin-1-oxyl (TEMPO) - Prior Art | 10 | 4.14 | 20.4 | 0.50 | 6.7 | 0 |
|  | 15 | 0.98 | 22.3 | 0.45 | 77 | 0 |
|  | 18 | 0 | 23.4 | 0.22 | 100 | 0 |
|  | 25 | 0 | 23.8 | 0.23 | 100 | 0 |
|  | 50 | 0 | 24.05 | 0.22 | 100 | 0 |
|  | 200 | 0 | 23.8 | 0.25 | 100 | 0 |
| 4-hydroxy-2,2,6,6-tetramethylpiperidin-1-oxyl (TEMPO) and TIPA (Invention Composition-2) | 5 + 1 | 1.2 | 19.6 | 0.45 | 75.2 | 3.9 |
|  | 7.5 + 1.5 | 0 | 22.95 | 0.19 | 100 | 0 |
|  | 8 + 1 | 0 | 22.4 | 0.25 | 100 | 0 |
|  | 10 + 0.5 | 2.19 | 19.46 | 0.53 | 50.7 | 4.6 |
|  | 10 + 1 | 0 | 21.7 | 0.32 | 100 | 0 |
|  | 200 + 10 | 0 | 13.1 | 0.21 | 100 | 36.1 |
|  | 200 + 50 | 0 | 10.5 | 0.35 | 100 | 48.5 |

The above experiment of Invention Composition—1 of Table 1 confirms that with addition of just 1.5 ppm of TIPA, only 17 ppm of QM is required as against 200 ppm of QM to achieve 100% control/inhibition of polymerization of 1,3-butadiene, thereby results in saving of about 183 ppm (about 91.5%) of QM confirming surprising and unexpected technical advantages of the present composition.

Experiment—II.
Condition: Autoclave (100 ml Capacity)
Sample: 1,3-Butadiene (without deep tube cylinder)
Temperature: 140° C.
Time: Varies
Motor speed: 1000 rpm Purge gas: Nitrogen (15 kgs Blanketing, pressure at 140° C. is 48-49 kgs).

TABLE II

| Additive | Time, hrs | Active Dosage (ppm) | Gel (%) | Di-mer (%) | Non Vola-tile (%) | % Efficiency of Polymer-ization control |
|---|---|---|---|---|---|---|
| Blank | 1 | — | 0 | 14.9 | 0.55 | — |
|  | 2 | — | 6.4 | 23.2 | 0.35 | — |
|  | 4 | — | 14.25 | Nil | — | — |
| 4-benzylidene-2,6-di-tert-butylcyclohexa-2,5-dienone (QM) - Prior art | 4 | 50 | 8.0 | 20.4 | 0.48 | 43.9 |
| 4-benzylidene-2,6-di-tert-butylcyclohexa-2,5-dienone (QM) and TIPA - (Invention Composition-1) | 4 | 40 + 10 | 3.2 | 23.6 | 0.22 | 77.5 |
|  | 4 | 55 + 5 | 2.2 | 23.0 | 0.55 | 84.6 |
|  | 4 | 60 + 15 | 0 | 25.9 | 0.45 | 100 |
| 4-hydroxy-2,2,6,6-tetramethylpiperidin-1-oxyl (TEMPO - Prior art | 4 | 50 | 3.4 | 25.8 | 0.33 | 76.1 |
|  | 4 | 60 | 0.8 | 30.6 | 0.50 | 94.4 |
|  | 4 | 75 | 0 | 30.9 | 0.4 | 100 |
| 4-hydroxy-2,2,6,6-tetramethylpiperidin-1-oxyl (TEMPO) and TIPA - (Invention Composition-2) | 4 | 40 + 10 | 0 | 30.1 | 0.19 | 100 |

The above experiment of Invention Composition—1 of Table 2 confirms that with the present composition comprising 60 ppm of QM and 15 ppm of TIPA, 100% control/inhibition of polymerization of 1,3-butadiene is achieved, and with the present composition comprising 55 ppm of QM and 5 ppm of TIPA, about 84.6% control/inhibition of polymerization of 1,3-butadiene is achieved, and with the present composition comprising 40 ppm of QM and 10 ppm of TIPA, about 77.5% control/inhibition of polymerization of 1,3-butadiene is achieved as against about 43.9% controller/inhibition of polymerization of 1,3-butadiene when 50 ppm of prior art additive is used, which confirms surprising and unexpected technical advantages of the present composition.

The above experiment of Invention Composition—2 of Table 2 confirms that with addition of just 10 ppm of TIPA, only 40 ppm of TEMO is required as against 75 ppm of TEMPO to achieve 100% control/inhibition of polymerization of 1,3-butadiene, thereby results in saving of 35 ppm (about 46.6%) of TEMPO, and when the prior art additive is used, then only 76.1% control/inhibition of polymerization of 1,3-butadiene is achieved, which also confirms surprising and unexpected technical advantages of the present composition.

Accordingly, all of above experimental findings confirm that a solution to the industrial problems of controlling and inhibiting polymerization of butadiene, and additionally controlling dimerization of butadiene with reduced or minimized amounts of the prior art additives has been achieved.

Further, the above experimental findings also confirm synergistic, surprising and unexpected effects of the presently provided compositions.

All of the above experiments also confirm that the present compositions are capable of achieving far better efficiency to control and inhibit polymerization of monomers stream comprising butadiene and excluding aromatic monomers, and additionally controlling dimerization of butadiene with same dosage of the prior art additives, meaning thereby, the present invention results in economical and environmental benefits.

The above experimental results also confirm that the presently provided compositions are far superior than prior art additives, and hence, have technical advantages and surprising effects over the prior art additives.

It may also be noted that the term "about" appearing before value or range of value and as employed herein is not intended to enlarge scope of the corresponding value or range of value, and the claimed invention, but is intended to include, within scope of the present invention, experimental errors permissible in the field of the invention.

It may also be noted that the present invention has been described with the help of foregoing experiments which have been performed on the laboratory scale. It is obvious to the persons skilled in the art to modify the present invention to apply it to industrial scale without deviating from its scope, and such application of present invention is included in its scope.

The invention claimed is:

1. Additive composition for control and inhibition of polymerization of aliphatic monomers including butadiene and for control and inhibition of dimerization of aliphatic monomers including butadiene consisting of:
    A) one or more first component comprising:
        a) quinone methide (QM),
        b) quinone methide (QM) derivative including ester derivative of quinone methide,
        c) nitroxide compounds, or
        d) a mixture thereof;
    and
    B) one or more second component selected from amines or polyamines, wherein the amine or polyamine comprises:
        i) oxide treated tertiary amines,
        ii) hydroxyl alkyl tertiary amines,
        iii) polyether amines, or
        iv) a mixture thereof.

2. The additive composition as claimed in claim 1, wherein the oxide treated tertiary amine comprises N,N,N',N'-Tetrakis (2-hydroxypropyl) ethylene-diamine (Quadrol®).

3. The additive composition as claimed in claim 1, wherein the hydroxyl alkyl tertiary amine comprises tris(2-hydroxypropyl)amine (TIPA).

4. The additive composition as claimed in claim 1, wherein the nitroxide compound comprises 1-oxyl-2,2,6,6-tetramethylpiperidin-4-ol (4HT).

5. The additive composition as claimed in claim 1, wherein the composition comprises;
    a) 40 to 99.75% by weight of I) one or more of said first component; and
    b) 0.25 to 60% by weight of II) said second component.

6. The additive composition as claimed in claim 1, wherein amount of the composition comprises the amount varying from 0.01 ppm to 2000 ppm, or from 1 ppm to 2000 ppm by weight of the stream of the aliphatic monomers including the butadiene.

7. The additive composition as claimed in claim 1, wherein the stream excludes aromatic monomers.

8. A method of using additive composition for controlling and inhibition of polymerization of aliphatic monomers including butadiene and for controlling and inhibition of dimerization of aliphatic monomers including butadiene, wherein to stream of the aliphatic monomers including the butadiene the additive composition consisting of:

A) one or more component A comprising:
  a) quinone methide (QM),
  b) quinone methide (QM) derivative including ester derivative of quinone methide,
  c) nitroxide compounds, or
  d) a mixture thereof;
and
B) one or more component B selected from amines or polyamines, wherein said amine or polyamine comprises:
  i) oxide treated tertiary amines,
  ii) hydroxyl alkyl tertiary amines,
  iii) polyether amines, or
  iv) a mixture thereof,
is added.

9. The method as claimed in claim 8, wherein the oxide treated tertiary amine comprises N,N,N',N'-Tetrakis (2-hydroxypropyl) ethylene-diamine (Quadrol®).

10. The method as claimed in claim 8, wherein the hydroxyl alkyl tertiary amine comprises tris(2-hydroxypropyl)amine (TIPA).

11. The method as claimed in claim 8, wherein the nitroxide compound comprises 1-oxyl-2,2,6,6-tetramethyl-piperidin-4-ol (4HT).

12. The method as claimed in claim 8, wherein the composition comprises:
  a) 40 to 99.75% by weight of I) one or more of said component A; and
  b) 0.25 to 60% by weight of II) said component B.

13. The method as claimed in claim 8, wherein amount of the composition added to the stream of the aliphatic monomers including the butadiene comprises the amount varying from 0.01 ppm to 2000 ppm, or from 1 ppm to 2000 ppm by weight of the stream.

14. The method as claimed in claim 8, wherein the stream excludes aromatic monomers.

15. A method for controlling and inhibition of polymerization of aliphatic monomers including butadiene and for controlling and inhibition of dimerization of aliphatic monomers including butadiene, wherein said monomers are treated with the additive composition consisting of:
A) one or more component A comprising:
  a) quinone methide (QM),
  b) quinone methide (QM) derivative including ester derivative of quinone methide,
  c) nitroxide compounds, or
  d) a mixture thereof;
and
B) one or more component B selected from amines or polyamines, wherein said amine or polyamine comprises:
  i) oxide treated tertiary amines,
  ii) hydroxyl alkyl tertiary amines,
  iii) polyether amines, or
  iv) a mixture thereof.

16. The method as claimed in claim 15, wherein the oxide treated tertiary amine comprises N,N,N',N'-Tetrakis (2-hydroxypropyl) ethylene-diamine (Quadrol®).

17. The method as claimed in claim 15, wherein the hydroxyl alkyl tertiary amine comprises tris(2-hydroxypropyl)amine (TIPA).

18. The method as claimed in claim 15, wherein the nitroxide compound comprises 1-oxyl-2,2,6,6-tetramethyl-piperidin-4-ol (4HT).

19. The method as claimed in claim 15, wherein the composition comprises:
  a) 40 to 99.75% by weight of I) one or more of said component A; and
  b) 0.25 to 60% by weight of II) said component B.

20. The method as claimed in claim 15, wherein amount of the composition added to the stream of the aliphatic monomers including the butadiene comprises the amount varying from 0.01 ppm to 2000 ppm, or from 1 ppm to 2000 ppm by weight of the stream.

21. The method as claimed in claim 15, wherein the stream excludes aromatic monomers.

22. The method as claimed in claim 15, wherein the temperature of the polymerization comprises the temperature varying from 50 degree C. to 180 degree C., or from 60 degree C. to 180 degree C.

23. A method for preparation of additive composition of claim 1 for controlling and inhibition of polymerization of aliphatic monomers including butadiene and for controlling and inhibition of dimerization of aliphatic monomers including butadiene, wherein the method comprises:
(A) mixing one or more said component A comprising:
  a) quinone methide (QM),
  B) quinone methide (QM) derivative including ester derivative of quinone methide,
  c) nitroxide compounds, or
  d) a mixture thereof;
with
B) one or more said component B selected from amines or polyamines, wherein said amine or polyamine comprises:
  i) oxide treated tertiary amines,
  ii) hydroxyl alkyl tertiary amines,
  iii) polyether amines, or
  iv) a mixture thereof.

* * * * *